(12) United States Patent
Li (10) Patent No.: US 7,745,131 B2
(45) Date of Patent: Jun. 29, 2010

(54) **HIGH THROUGHPUT GENOME SPECIFIC MOLECULAR MARKERS FOR ERUCIC ACID CONTENT GENES IN *BRASSICA NAPUS***

(76) Inventor: Genyi Li, c/o Technology Transfer Office, 631 Drake Centre, Winnipeg Manitoba (CA) R3T 5V4

( * ) Notice: Subject to any disclaimer, the term of this patent is extended or adjusted under 35 U.S.C. 154(b) by 104 days.

(21) Appl. No.: 11/965,936

(22) Filed: Dec. 28, 2007

(65) Prior Publication Data

US 2008/0160530 A1     Jul. 3, 2008

Related U.S. Application Data

(60) Provisional application No. 60/882,332, filed on Dec. 28, 2006.

(51) Int. Cl.
*C12Q 1/68* (2006.01)
*C12P 19/34* (2006.01)
*C07H 21/02* (2006.01)
*C07H 21/04* (2006.01)

(52) U.S. Cl. .................. 435/6; 435/91.2; 536/23.1; 536/23.72; 536/24.3; 536/24.33

(58) Field of Classification Search ................. None
See application file for complete search history.

(56) References Cited

U.S. PATENT DOCUMENTS

2004/0106122 A1*   6/2004   Wilmer et al. ................ 435/6

FOREIGN PATENT DOCUMENTS

WO    WO 2005/058019    *   6/2005

OTHER PUBLICATIONS

NCBI Database, National Center for Biotechnology Information, National Library of Medicine, NIH (Bethesda, MD,USA) GenBank Accession No. BZ499865, Dec. 16, 2002.*

Katavic et al. European Journal of Biochem. 2002. 269: 5625-5631.*
Fourmann et al. Theor Appl Genet. 1998. 96: 852-858.*
Applied Biosystems. Protocol for ABI PRISM® SNaPshot Multiplex Kit. 2000, Applied Biosystems, Foster City, California, USA.*

* cited by examiner

*Primary Examiner*—Carla Myers
(74) *Attorney, Agent, or Firm*—MIchael R. Williams; Ade & Company Inc (57) ABSTRACT

A single base change in the Bn-FAE1.1 gene in the A genome and a two-base deletion in the Bn-FAE1.2 gene in the C genome produce the nearly zero content of erucic acid observed in canola. A BAC clone anchoring Bn-FAE1.1 from a *B. rapa* BAC library and a BAC clone anchoring Bn-FAE1.2 from a *B. oleracea* BAC library were used in this research. After sequencing the gene flanking regions, it was found that the dissimilarity of the flanking sequences of these two FAE1 homologs facilitated the design of genome specific primers that could amplify the corresponding genome in allotetraploid *B. napus*. The two-base deletion in the C genome gene was detected as a sequence characterized sequence region (SCAR) marker. To increase the throughput, one genome specific primer was labeled with four fluorescence dyes and combined with 20 different primers to produce PCR products with different fragment sizes. Eventually, a super pool of 80 samples was detected simultaneously, making it possible to analyze over half a million of samples per day using a medium capacity ABI 3100 Genetic Analyzer. This dramatically reduces the cost of marker detection. The single base change in the Bn-FAE1.1 gene was detected as single nucleotide polymorphic (SNP) marker with an ABI SNaPshot kit. A multiplexing primer set was designed by adding a polyT to the 5' primer end to increase SNP detection throughput through sample pooling. These multiplexed high throughput molecular markers have been successfully implemented in our canola/rapeseed breeding programs.

1 Claim, 2 Drawing Sheets

1. Upstream flanking region

```
FAEA    AAATTATCTTATTCCGGTCATGTTGGCCTTAACTAAAC TTCCACACATTTGTTTA- CTGA-
FAEC    ATGTGGTGACACGT-GGTTTGAAACCCACCAAATAATCGATCACAAAAAACCTAAGTTAA
         *  *   *    *   ** *       *     ** ***   *    ****  *    ** * * *

FAEA    TATTCG AGTATAAACTTTGCGGGAAAACTCATTCCCGAGAAACACTGATCCCATAATTAG
FAEC    GGATCGGTAATAACCTTT CTAATTAAT TTTGATTTAATT AAA- TCACTCTTTT TA TTTA
          * **     * * * *  * * **            * *    *     *       * *   * * *

FAEA    TCAGAGTCTATGTCGGTTTAGCCTATC- ACTG- CTAAGTACAAAAATTCTCTCGAATTCA
FAEC    T- AAACCCCACTAAATTATGCGATATTGATTGTCTAAGTACAAAAATTCTCTCGAATTCA
        *  *   *    *  *        * *   * ** ** *** * * * * * ** ** * ** ** * * *
```

2. Downstream flanking region

```
FAEA    GTATGTATCTCTTA --- --- -TTTA - - CATGAAA - - -TTTTTAAACGCCT - - - -AACACT
FAEC    GTATGTATCTCTTAGACCATCTTTAACCCTAAAACCCTTTTTGAGATCCTTAAGAAAATT
        ** * * **  ** ** * ** * **       * *** *  * *   * **    * ****  *   ** *      ** * *

FAEA    ATGACGTCATATCCTAAATCAAACAA - -CTAAAACCCCGAGTT - - - - - -CTATCATTTAT
FAEC    TTAATAATAAATTAAACCTTAAGTGGGGTTAAGGATCTC TGTTAAGAAACTTCCATTTTT
         *  *       *   **     *    * **      * **      ** *        * **      ** * ****  *
```

HIGH THROUGHPUT GENOME SPECIFIC MOLECULAR MARKERS FOR ERUCIC ACID CONTENT GENES IN BRASSICA NAPUS

PRIOR APPLICATION INFORMATION

The instant application claims the benefit of U.S. Provisional Patent Application 60/882,332, filed Dec. 28, 2006.

BACKGROUND OF THE INVENTION

Canola/rapeseed (Brassica napus L.) is a major oilseed crop in Canada, Europe, Australia, China and the Indian subcontinent. The quality of canola/rapeseed oil is determined primarily by its constituent fatty acids. The major fatty-acid constituents of Brassica oil are palmitic acid (C16:0), stearic acid (C18:0), Oleic (C18:1), linoleic acid (C18:2), linolenic acid (C18:3), arachidic acid (C20:0), eicosenoic acid (C20:1), erucic acid (C22:1). Erucic acid is one of the main fatty acids in rapeseed oil. Low erucic acid in rapeseed improves the quality of the oil because high erucic acid is relatively low in digestibility and has been associated with health problems (Beare et al. 1963). On the other hand, high erucic acid rapeseed (HEAR) has several potential applications in the oleo-chemical industry for the production of high temperature lubricants, nylon, plastics, slip and coating agents, soaps, painting inks, surfactants (Topfer et al. 1995).

In B. napus, additive alleles at two gene loci control the erucic acid content in seeds (Harvey and Downey 1964), and these two genes (E1 and E2) are mapped in rapeseed (Ecke et al. 1995; Jourdren et al. 1996; Thormann et al. 1996). Development of low or high erucic acid content B. napus cultivars requires a long process of crossing, backcrossing and selfing of the segregating generations followed by identification of low or high erucic acid content lines from fatty acid profiles of seed lots from individual seeds by gas chromatography (GC). However, DNA molecular markers which are tightly linked to the erucic acid genes or inside the candidate genes can be applied with high efficiency in marker assisted selection (MAS) for rapid transfer of a character into an otherwise desirable genotype efficiently and effectively. For instance, 15 of 16 plants in the $F_2$ generation of canola/rapeseed crosses could be discarded at the seedling stage by selecting homozygous Bn-FAE1.1 and Bn-FAE1.2 genotypes with high or low erucic acid content instead of growing plants to full maturity and then doing seed quality analysis and selection.

The pathway for erucic acid biosynthesis and the major reactions involved in this pathway has been well characterized in Arabidopsis. Oleic acid is the main precursor for erucic acid biosynthesis via an elongation process in the developing embryos of B. napus (Xiaoming et al, 1998). In seeds of Arabidopsis thaliana it was reported that fatty acid elongase 1 (FAE1) is the candidate gene and that the gene product was essential for elongation of C18:1 (oleic acid) to C22:1 (erucic acid) (Lemieux et al. 1990; Kunst et al. 1992). The elongation process has four different steps. The first step is the condensation of oleoyl-CoA to malonyl-CoA to form a 3-ketoacyl-CoA. The second step is the reduction of the 3-ketoacyl-CoA to produce 3-hydroxyacyl-CoA. The third step is the dehydration of the 3-hydroxyacyl-CoA to form trans-(2,3)-enoyl-CoA. The final step it is the further reduction of the trans-(2,3)-enoyl-CoA. These reactions are catalyzed by four different enzymes 3-ketoacyl-CoA synthase, 3-ketoacyl-CoA reductase, 3-hydroxyacyl-CoA dehydratase and trans-(2,3)-enoyl-CoA reductase, respectively (Fehling and Mukherjee 1991). The role of FAE1 gene in producing erucic acid was genetically ascertained by genetic transformation of a low erucic acid content rapeseed (Lassner et al. 1996). In rapeseed, the two loci E1 and E2 of FAE1 homologs encode the rapeseed 3-ketoacyl-CoA synthases for the elongation process to generate erucic acid from oleoyl-CoA (Barret et al. 1998 and Fourmann et al. 1998). In B. napus, these two homologs of the FAE1 gene (Bn-FAE1.1 and Bn-FAE1.2) have been characterized. These two homologs show 99.4% nucleotide identity and a two-base deletion in the low erucic acid content line results in a functional loss of Bn-FAE1.2 gene in the C genome (Fourmann et al. 1998). Katavic et al. (2002) reported that single amino acid serine at 282 positions in high erucic acid content line is substituted by phenylalanine in low erucic acid content line due to one base change in the Bn-FAE1.1 gene in the A genome. In this report, BAC clones containing Bn-FAE1.1 and Bn-FAE1.2 genes from the A and C genome libraries were used to extend the sequence on the outside of these two genes to develop genome specific high throughput molecular markers. These markers will considerably facilitate the selection of the four different erucic acid content control alleles in canola/rapeseed breeding programs.

SUMMARY OF THE INVENTION

According to an aspect of the invention, there is provided a method of identifying the erucic acid locus in a Brassica plant comprising:

admixing at least one of the primers of Table 1 with DNA from a Brassica plant under conditions suitable for nucleic acid extension; and analyzing the extension product produced from a given DNA sample, wherein a single extension product having a first length indicates that the erucic acid locus is homozygous high erucic acid content, a single extension product having a second length indicates that the erucic acid locus is homozygous low erucic acid content and two extension products of both first and second lengths indicates that the erucic acid locus is heterozygous.

According to another aspect of the invention, there is provided a method for determining the erucic acid content of a Brassica napus plant cell comprising:

determining the genotype of a Brassica napus plant cell at the Bn-FAE1.1 and Bn-FAE1.2 loci, wherein a C to T substitution at position 846 of Bn-FAE1.1 and a two nucleotide deletion at position 1425-1426 of Bn-FAE1.2 indicates low erucic acid content.

DESCRIPTION OF THE PREFERRED EMBODIMENTS

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

In rapeseed, the wild type genotypes produce high erucic acid content in the seed. Low erucic acid content genotypes possess mutations affecting both E1 and E2 loci controlling erucic acid content in the seed (Harvey and Downey, 1964). The fatty acid elongation 1 (FAE1) encoding 3-ketoacyl-CoA synthase has been characterized in Arabidopsis thaliana (James et al 1995) and jojoba (Lassner et al. 1996). Barret et al. (1998) identified the FAE1 gene in Brassica napus with two homologous sequences (Bn-FAE1.1 and Bn-FAE1.2) from the embryo. The Bn-FAE1.1 gene has been shown to be linked to the E1 locus for B. rapa, and Bn-FAE1.2 was assigned to the E2 locus in B. oleracea. Only three nucleotide changes, a single base change in Bn-FAE1.1 and a two-base deletion in Bn-FAE1.2 account for the fatty acid difference of canola and rapeseed (Barret et al., 1998; Fourmann et al., 1998, Katavic et al. 2002). By targeting these three base changes, high throughput gene-specific markers for both BnFAE1.1 and Bn-FAE1.2 were developed. These markers are perfect matches with erucic acid content and no recombination occurs between the markers and trait.

Sequence similarity among the homologous genes in the A and C genes in B. napus is very high for most genes even in intergenic regions, which is an obstacle for developing gene specific markers. The Bn-FAE1.1 gene in the A genome and the Bn-FAE1.2 gene in the C genome have similar sequence similarities. Since the sequence similarity of these two genes is very high, it is difficult to amplify the SNP position for low ER in the A genome, because the same gene sequence is present in the C genome for high erucic acid content. Similarly, it is difficult to separately amplify the two-base deletion mutation for low erucic content genotypes in the C genome, because the same gene sequence is present in the A genome for high erucic acid which hinders the identification of genotypes with homozygous deletion alleles. To overcome these problems, the extended sequence from the flanking regions of Bn-FAE1.1 in the A genome and Bn-FAE1.2 in the C genome were determined. Sequence dissimilarities outside the genes regions in the A and C genomes were large enough for genome-specific primers to amplify the A genome specific Bn-FAE1.1 containing a SNP position and the C genome specific Bn-FAE1.2 containing a two-base deletion position. This is the first reported approach to amplify the A and C genome specific FAE1 genes in B. napus for precise tagging of the high and low erucic acid content genotypes in B. napus.

Increasing throughput and reducing the cost for molecular marker detection is critical for large scale application of MAS in canola/rapeseed breeding programs since large number of plants have to be screened in a short time. In this report, multiplexed SNP detection and multiplexed SCAR markers were demonstrated using a series of SNP detection primers varying in size by adding polyT at the primer 5' end. Twenty two SNP detection primers allow a mixture of 22 reactions in one well. In theory, 17600 samples (22×16×50) can be done with a medium throughput DNA analyzer, such as ABI 3100 DNA analyzer, within 24 hrs. Similarly with an ABI 3100 Genetic analyzer, over half a million (4×20×16×48) samples can be detected with the SCAR markers for Bn-FAE1.2 within 24 hrs since the genome specific primer labeled with four fluorescent dye colors can be used in our laboratory. Using this approach it is possible to pool 80 PCR products for detection in an ABI genetic analyzer which could reduce running time and cost by approximately 80 times.

The ABI 3100 genetic analyzer can be used with high efficiency to detect two-base difference markers. The two base deletion in the C genome could also be detected using SNaPshot, but using a SCAR marker is much cheaper than using SNaPshot since only a small amount of specific PCR product is required for detection. Additionally it is a one step PCR with a short PCR amplification program, about 15-20 cycles. Approximately 500,000 samples could be done with a medium throughput DNA analyzer and three million samples could be done with a high throughput DNA analyzer, such as ABI 3700 genetic analyzer, within 24 hrs, with a per sample cost of just a few cents instead of more than one dollar.

Thus, in one aspect of the invention, there is provided a method for determining the erucic acid content of a plant cell comprising determining the genotype of the plant cell at the Bn-FAE1.1 and Bn-FAE1.2 loci, wherein a C to T substitution at position 846 of Bn-FAE1.1 and a two nucleotide deletion at position 1425-1426 of Bn-FAE1.2 indicates low erucic acid content.

In a preferred embodiment of the invention, a portion of the Bn-FAE1.1 locus is first amplified using FEAG4 (SEQ ID No. 1) and FEAS12O (SEQ ID No. 2) or FEAF1 (SEQ ID No. 3). Once this region has been amplified using means known in the art, the single base substitution at position 846 can be determined using means known in the art, as discussed below. In a preferred embodiment, a SNP detection primer selected from FEAF1-FEAF22 (SEQ ID Nos. 3-24) is utilized.

In a preferred embodiment of the invention, a portion of the Bn-FAE1.2 locus is first amplified using FE42A (SEQ ID No. 25) and a primer selected from SEQ ID Nos. 26-45 as shown in Table 1. As discussed below, when paired with FE42A (SEQ ID No. 25), the respective primers designated SEQ ID Nos. 26-45 each produce products of different length, but in all cases will produce two products differing in length by two nucleotides when the Bn-FAE1.2 locus is heterozygous within the cell as discussed below. As will be appreciated by one of skill in the art, selection of a specific primer to pair with FE42A is accordingly a matter of choice and will depend on reaction and resolution conditions.

According to an aspect of the invention, there is provided a method of identifying the erucic acid locus in a Brassica plant comprising:

admixing at least one of the primers of Table 1 with DNA from a Brassica plant under conditions suitable for nucleic acid extension; and analyzing the extension product produced from a given DNA sample, wherein a single extension product having a first length indicates that the erucic acid locus is homozygous high erucic acid content, a single extension product having a second length indicates that the erucic acid locus is homozygous low erucic acid content and two extension products of both first and second lengths indicates that the erucic acid locus is heterozygous.

Results

Study on Erucic Acid Content of *B. napus*

Self-pollinated seeds of 279 $F_2$ and 159 $BC_1$ plants from a cross of 'MillenniUM03' and 'SRYS-3', were examined for erucic acid content. The parental lines, 'MillenniUM03' and 'SRYS-3', have 56% and 0% erucic acid in seed, respectively. Twenty out of 279 plants produced low erucic content in $F_2$, and 39 out of 159 $BC_1$ plants showed low erucic acid content in seed. These results were consistent with a digenic (15:1 for $F_2$ and 3:1 for $BC_1$) segregation ratio indicating that two genes are responsible for erucic acid content (Table 2).

Gene Specific SNP Markers for Bn-FAE1.1 in the A Genome in *B. napus*

Figure 1:
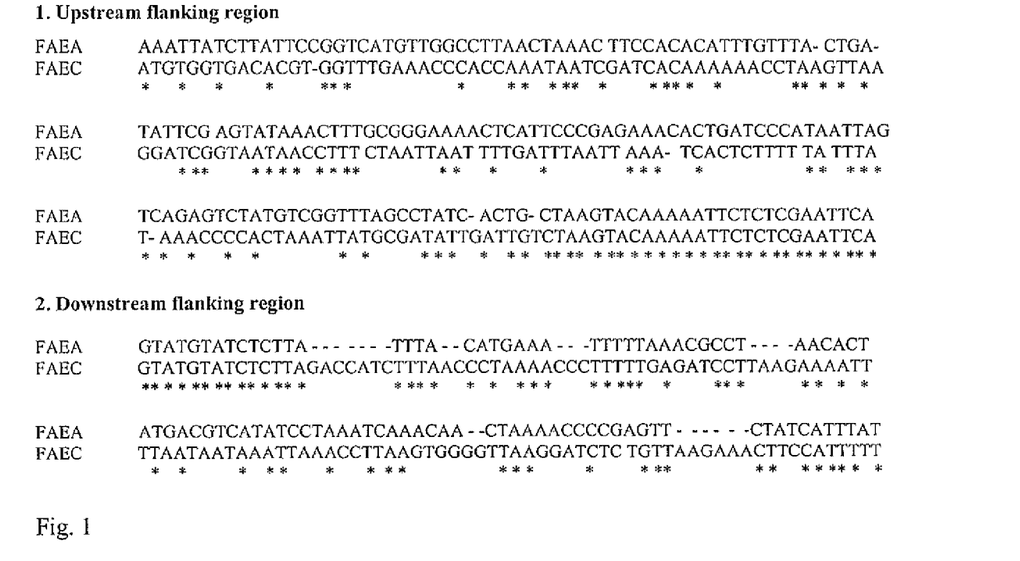
FIG. 1 The upstream and downstream sequence comparison of the Bn-FAE1.1 and the Bn-FAE1.2 genes in the A-genome, B. rapa, and C-genome B. oleracea, respectively. SEQ ID No. 46 is the Brassica rapa upstream sequence, SEQ ID No. 47 is the Brassica rapa downstream sequence, SEQ ID No. 48 is the Brassica oleracea upstream sequence and SEQ ID No. 49 is the Brassica oleracea downstream sequence.
Figure 2:
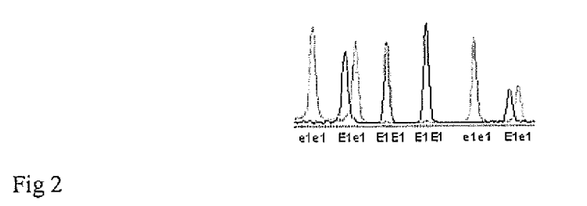
FIG. 2 Showing multiplexed SNP detection by GeneScan software in ABI 3100 genetic analyzer to analyze the SNaPshot data. The peak information has been transformed manually for each loci [e.g. black for 'C' and the genotype is E1E1; grey for 'T' and genotype is e1e1; and black/grey for 'C/T' and genotype E1e1].

Gene specific markers for the A-genome (Bn-FAE1.1 gene) were developed by targeting a transition type base substitution at position 846 (C to T) from the starting codon in low erucic acid content lines. Because of the high level of sequence conservation between Bn-FAE1.1 and Bn-FAE1.2, some primers targeting the sequence dissimilarities between the Bn-FAE1.1 and Bn-FAE1.2 coding regions were found to be unreliable to produce genome specific PCR products. In order to design reliable primers for genome specific PCR products, chromosome walking 2.5 kb upstream and 1.5 kb downstream of the flanking sequence of the Bn-FAE1.2 gene from the broccoli BAC clone, and 750 by upstream and 700 by downstream flanking sequences of the Bn-FAE1.1 gene from the *B. rapa* BAC clone was conducted. After Clustalw analysis, dissimilarities between the upstream and downstream flanking sequences of Bn-FAE1.1 and Bn-FAE1.2 genes were found (FIG. 1). On the basis of these dissimilar sequences, one primer FEAG4 in the upstream flanking region and another primer FEAF1 inside the gene were designed to amplify a 1.2 kb A-genome specific fragment containing the single nucleotide polymorphic (SNP) position. The SNP was detected by using single base extension method with ABI SNaPshot Multiplex kit. The SNaPshot data were analyzed by GeneScan software and peak information was transformed manually for each loci. The polymorphic position containing homozygous 'C' for high erucic acid content exhibited a black peak, homozygous 'T' for low erucic acid content, a grey peak, and 'C|T' for heterozygous plants, both a black peak and a grey peak (FIG. 2). Genotypes were assigned accordingly with E1E1 for the black peak, e1e1 for the grey peak and E1e1 for both the black peak and the grey peak. One hundred and seventy four $F_2$ plants were tested for the Bn-FAE1.1 gene using SNaPshot. In this $F_2$ population, 43 plants exhibited the E1E1 genotype, 81 showed the E1e1 genotype and 50 showed the e1e1 genotype, a good fit to a 1:2:1 genotypic ratio for single locus segregation for the Bn-FAE1.1 gene ($X^2$=1.385, P=0.2-0.3). Similarly, in the $BC_1$ population 49 plants were found to be the E1e1 genotype and 59 were the e1e1 genotype, consistent with the 1:1 expected genotypic segregation for a single locus inheritance for Bn-FAE1.1 gene ($X^2$=0.926, P=0.3-0.5).

Gene Specific SCAR Markers for the Bn-FAE1.2 Gene in the C Genome in *B. napus*

Figure 3A:
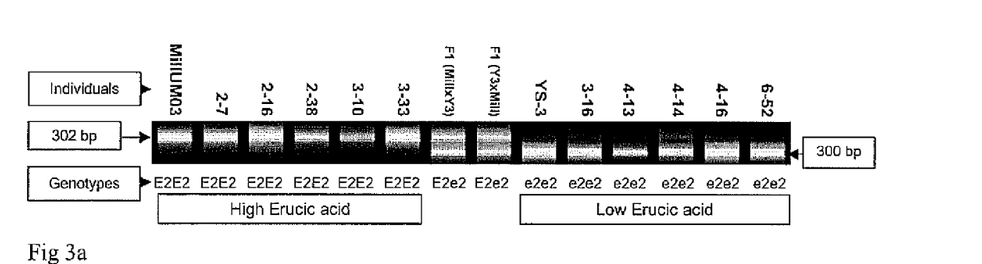
FIG. 3a Detection of C-genome specific High ER, $F_1$, $F_1'$ and low ER lines using C-genome specific primers FE42A/FE42F. The upper band is responsible for high ER (E2E2), lower band is for low ER (e2e2) and double band is for intermediate ER (E2e2).
Figure 3B:
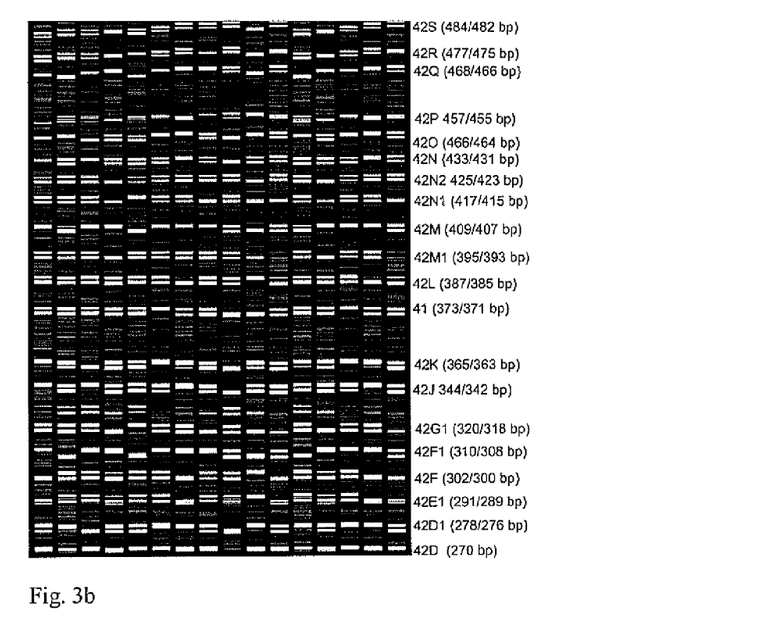
FIG. 3b Identification of different erucic acid content segregating populations using labeled FE42A primer with twenty different upstream unlabelled primers to produce various DNA fragments from 270 bp to 484 bp. The upper band is two bases larger than the lower band for all pairs.

Gene specific markers for the Bn-FAE1.2 gene in the C genome were developed after the genome specific primers were designed. The two-base deletion is located at 1425-1426 bp position for low erucic acid content lines which result in a truncated protein due to an early stop codon (Fourmann et al. 1998). Fortunately, this deletion was close to the down stream dissimilarity region where a C genome specific primer FE42A (SEQ ID No. 25) was designed. Twenty different primers (SEQ ID Nos. 26-45) within the gene coding region from the upstream of the polymorphic region (CAAAT/CAT) were also designed to amplify various fragments of varying from 270 bp to 484 bp in size. The DNA fragment specific for high erucic acid content lines consistently produced two-base larger fragments than those of low erucic acid content lines. This small difference was easily detected by the ABI 3100 Genetic Analyzer when the primer FE42A was labeled with a fluorescent dye. Therefore, the Bn-FAE1.2 gene for homozygous high erucic acid content lines generated two-base larger fragments, the low erucic acid content lines had two-base smaller fragments and the heterozygous lines had both larger and smaller fragments (FIG. 3a). Since these twenty different primers combinations generated fragments that were different in size, it was possible to pool the PCR products from 20 different primer combinations to achieve multiplexed, high throughput markers. With one fluorescent dye color, 320 DNA samples (16×20) were separated in one run in 30 minutes with the ABI 3100 DNA analyzer (FIG. 3b).

A total of 174 $F_2$ plants were analyzed for the Bn-FAE1.2 gene in the C genome. Of these, 46 were E2E2 genotype (single upper band for high ER), 45 were e2e2 genotype (single lower band for low ER) and 83 were E2e2 genotype (both upper and lower band for intermediate band). The $F_2$ population fit a 1:2:1 genotypic ratio for single locus inheritance for Bn-FAE1.2 for high, intermediate and low erucic acid content alleles ($\chi^2$=0.378, P=0.5-0.7). Similarly, 108 $BC_1$ plants segregated into two groups, 51 for the E2e2 genotype and 57 for the e2e2 genotype which also fit a 1:1 genotypic ratio for single locus segregation for Bn-FAE1.2 ($\chi^2$=0.334, P=0.5-0.7).

Association of FAE1 Molecular Markers with Erucic Acid Content

Erucic acid content in the $F_2$ and $BC_1$ populations were associated with the two FAE1 homologs present in the A genome and the C genome. On the basis of SNP and SCAR markers, the $F_2$ plants were classified into nine different genotypes: E1E1E2E2, E1E1E2e2, E1E1e2e2, E1e1E2E2, E1e1E2e2, E1e1e2e2, e1e1E2E2, e1e1E2e2 and e1e1e2e2 for Bn-FAE1.1 and BN-FAE1.2 genes in the A genome and the C genome, respectively (FIGS. 2 and 3b, and Table 3). A total of 174 $F_2$ plants were tested for both genes, of which 10 were E1E1E2E2, 23 E1E1E2e2, 11 E1E1e2e2, 24 E1e1E2E2, 37 E1e1E2e2, 19 E1e1e2e2, 11 e1e1E2E2, 24 e1e1E2e2 and 15 e1e1e2e2 (Table 3). The segregation ratio was consistent with a 1:2:1:2:4:2:1:2:1 genotypic segregation ratio for two genes ($\chi^2$=2.091, P=>0.95). All genotypic classes were tested for erucic acid content in seeds and it was found that all four dominant alleles contributed to the highest erucic acid content with an average of 41.2%, three dominant alleles contributed an average of 34.4% (average E1E1E2=34.5% and average E1E2E2=34.3%), two dominant alleles contributed an average of 23.7% (E1E1=24.2%, E1E2=24.1% and E2E2=22.9%), one dominant allele contributed an average of 12.5% (E1=12.0% and E2=13.0%) while e1e1e2e2 plants had an average 0.26% erucic acid content (Table 3). The results indicated that all four alleles had almost identical contribution to erucic acid content in seed with an average of 11.2% erucic acid per allele.

A further study was conducted to test the association of the two genes with erucic acid content in 108 $BC_1$ plants developed from a cross of 'MillenniUM03' and 'SRYS-3', with 'SRYS-3' (low ER) as recurrent parent. The genotyping was done on the basis of SNP detection and two bases deletion detection in ABI 3100 genetic analyzer with four groups obtained from the $BC_1$ population as E1e1E2e2, E1e1e2e2, e1e1E2e2 and e1e1e2e2 (FIGS. 2 and 3b, and Table 3). Of the 108 BC$_1$ plants, 26 were E1e1E2e2 with an average 19.8% erucic acid content, 23 E1e1e2e2 with and average 10.5% erucic acid content, 22 e1e1E2e2 with an average 10.4% erucic acid content and 35 e1e1e2e2 with an average 0.18% erucic acid content. The four different genotypic classes fit a 1:1:1:1 backcross segregation ratio for two genes ($\chi^2$=3.373, P=0.3-0.5). The contributions of each allele for erucic acid content in seed in the BC$_1$ population were similar to each other at 10.2%.

Materials and Methods

Plant Materials

The pure breeding high erucic acid content cultivar 'MillenniUM03' (~55% erucic acid) was crossed with the pure breeding canola line 'SRYS-3' (0% erucic acid) and the F$_1$ was backcrossed to SRYS-3. The F$_1$, F$_2$, F$_3$ and BC$_1$ generations were grown in the greenhouse. Self-pollinated seeds of 279 F$_2$ and 159 BC$_1$ plants were examined for erucic acid content by gas chromatography (GC).

DNA Extraction and Sequencing of Flanking Sequence of the FAE1 Genes

DNA was extracted using a modified version of the CTAB method according to Li and Quiros (2001) from the flower buds of *B. rapa, B. oleracea, B. napus*. The broccoli BAC library and library screening strategy, as described by Quiros et al. (2001), was used to pick up the BAC clone anchoring the Bo-FAE1.2 gene. The *B. rapa* BAC library, constructed from a male sterile line (kindly provided by Dr. Quiros, University of California, Davis) was used to select the BAC clone containing the Br-FAE1.1 gene. BAC DNA was prepared from the A-genome library and the C-genome library of pooled cultures of all clones from each 384-well plate. Targeted positive clones from positive plates were identified using a column and row (24×16) pooling strategy. The primers were designed according the FAE1 sequence in the GenBank data (u50771, AF009563, Y14974, Y14975, Y14980). The flanking sequences of the FAE1 gene in the A-genome and C-genome were sequenced by primer walking with the selected BAC clones. With the extended flanking sequences, the polymorphic regions between the A-genome and C-genome were found and used to design genome specific primers.

Multiplexing SCAR Markers by Targeting the Two-Base Deletion in the Bn-FAE1.2 Gene The two-base deletion in the Bn-FAE1.2 gene is located at the end of this gene. With the extended 3'-end flanking sequence of Bn-FAE1.1 and Bn-FAE1.2, a polymorphic region was found and a genome specific primer FE42A targeting the Bn-FAE1.2 in the C genome was designed and another 20 primers were located inside the gene to form 20 primer pairs for multiplexing detection (Table 1). The genome specific primer was labeled with one of the four fluorescent dyes (6-FAM, VIC, NED and PET, ABI, California) and the PCR products in a range of 200 to 500 bp were separated with an ABI 3100 DNA analyzer (ABI, California).

SNaPshot Detection of the Bn-FAE1.1 Alleles

SNP markers were developed through targeting the single base change in the Bn-FAE1.1 gene in the A genome. A genome specific primers, 'FEAG4 and FEAS1' were designed on the basis of the extended gene flanking sequence to amplify the Bn-FAE1.1 gene in the A genome. For multiplexing, another 22 primers were designed to detect the single nucleotide polymorphism (SNP) in the Bn-FAE1.1 by adding polyT at the 5' end of the primers (Table 1).

The first step for SNP detection was to produce genome specific PCR products containing the SNP position. PCR reactions were performed in a 10 µl volume containing 60 ng of genomic DNA, 100 µM of each dNTP, 0.15 µM of each primer, 1×PCR buffer, 1.5 mM MgCl$_2$ and 1 Unit of Taq polymerase. The PCR program was: 94° C. for 3 min. followed by 35 cycles of 94° C. for 1.0 min, 55° C. for 1.0 min, 72° C. for 1.0 min and final extension 72° C. for 10 min.

SNP detection was performed using single nucleotide primer extension method in the ABI 3100 Genetic Analyzer using SNaPshot multiplex kit (ABI, California), following the instruction in the kit.

The SnaPshot products were pooled first and 2 µl pooled DNA was mixed with 8 µl formamide containing GeneScan™ 120 LIZ™ size standard (ABI, California). After the DNA was denatured for 5 minutes at 95° C., the DNA fragments were analyzed with an ABI 3100 Genetic Analyzer. Genotypes were scored manually, using peak color verification.

While the preferred embodiments of the invention have been described above, it will be recognized and understood that various modifications may be made therein, and the appended claims are intended to cover all such modifications which may fall within the spirit and scope of the invention.

REFERENCES

Barret P, Delourme R, Renard M, Domergue F, Lessire R, Delseny M, Roscoe T J (1998) Theor Appl Genet 96:177-186

Beare J L, Campbell J A, Youngs C G, Craig B M (1963) Effects of saturated fat in rats fed rapeseed oil. Can J Biochem Physiol 41:605-612

Ecke W, Uzunova M, Weileder K (1995) Mapping the genome of rapeseed (*Brassica napus* L.). II. Localization of genes controlling erucic acid synthesis and seed oil content. Theor Appl Genet 91: 972-977

Fehling E, Mukherjee K D (1991) Acyl-CoA elongase from higher plant (*Lunaria annua*): metabolic intermediates of very-longchain acyl-CoA products and substrate specificity. Biochim Biophys Acta 1082: 239-246

Fourmann M, Barret P, Renard M, Pelletier G, Delourme R, Brunel D (1998) The two genes homologous to *Arabidopsis* FAE1 co-segregate with the two loci governing erucic acid content in *Brassica napus*. Theor Appl Genet 96:852-858

Harvey B L, Downey R K (1964) The inheritance of erucic acid content in rapeseed (*Brassica napus*). Can J Plant Sci 44:104-111

James D W Jr, Lim E, Keller J, Plooy I, Ralston E, Dooner H K (1995) Directed tagging of the *Arabidopsis* Fatty Acid Elongation 1 (FAE1) gene with the maize transposon Activator. Plant Cell 7:309-319

Jourdren C, Barret P, Horvais R, Foisset N, Delourme R, Renard M (1996) Identification of RAPD markers linked to the loci controlling erucic acid level in rapeseed. Mol Breed 2:61-71

Katavic Vesna, Elzbieta Mietkiewska, Dennis L Barton, E Michael Giblin, Darwin W Reed, and David C Taylor (2002) Restoring enzyme activity in nonfunctional low erucic acid *Brassica napus* fatty acid elongase 1 by a single amino acid substitution. Eur J Biochem 269:5625-5631

Kunst L, Taylor D C, Underhill E W (1992) Fatty acid elongation in developing seeds of *Arabidopsis thaliana*. Plant Physiol Biochem 30: 425-434

Lassner M W, Lardizabal K, Metz J G (1996) A jojoba b-ketoacyl-CoA synthase cDNA complements the canola fatty acid elongation mutation in transgenic plants. Plant Cell 8:281-292

Lemieux B, Miquel M, Somerville C, Browse J (1990) Mutants of *Arabidopsis* with alterations in seed lipid fatty acid composition. Theor Appl Genet 80:234-240

Li G, Quiros C F (2001) Sequence related amplified polymorphism (SRAP) a new marker system based on a simple PCR reaction: its application to mapping and gene tagging in *Brassica*. Theor Appl Genet 103:455-461

Quiros C F, Grellet F, Sadowski J, Suzuki T, Li G, Wroblewski T (2001), *Arabidopsis* and *Brassica* comparative genomics: sequence, structure and gene content in the ABI-Rps2-Ck1 chromosomal segment and related regions. Genetics 157(3):1321-30.

Thormann C E, Romero J, Mantet J, Osborn T C (1996) Mapping loci controlling the concentrations of erucic and linolenic acids in seed oil of *Brassica napus* L. Theor Appl Genet 93:282-286

Topfer R, Nartini N, Schell J (1995) Modification of plant lipid synthesis. Science 268:681-686

Xiaoming Bao, Mike Pollard, John Ohirogge (1998) The Biosynthesis of Erucic Acid in Developing Embryos of *Brassica rapa*. Plant Physiol 118:183-190

TABLE 1

List of primers used in this experiment

Primers amplifying the A-genome specific fragment containing SNP position.

| | | |
|---|---|---|
| Forward: | | |
| FEAG4: | CTCATTCCCGAGAAACACTGA | (SEQ ID No. 1) |
| Reverse: | | |
| FEAS120: | CTACGATCTCCAGGCTTGTT | (SEQ ID No. 2) |
| SNP detection primers: | | |
| FEAF1: | TTTTTGCCGCTATTTTGCTCT | (SEQ ID No. 3) |
| FEAF2: | TTTTTTTTTGCCGCTATTTTGCTCT | (SEQ ID No. 4) |
| FEAF3: | TTTTTTTTTTTTTGCCGCTATTTTGCTCT | (SEQ ID No. 5) |
| FEAF4: | TTTTTTTTTTTTTTTTTGCCGCTATTTTGCTCT | (SEQ ID No. 6) |
| FEAF5: | TTTTTTTTTTTTTTTTTTTTTGCCGCTATTTTGCTCT | (SEQ ID No. 7) |
| FEAF6: | TTTTTTTTTTTTTTTTTTTTTTTTTGCCGCTATTTTGCTCT | (SEQ ID No. 8) |
| FEAF7: | TTTTTTTTTTTTTTTTTTTTTTTTTTTTTGCCGCTATTTTGCTCT | (SEQ ID No. 9) |
| FEAF8: | TTTTTTTTTTTTTTTTTTTTTTTTTTTTTTTTTGCCGCTATTTTGCTGT | (SEQ ID No. 10) |
| FEAF9: | TTTTTTTTTTTTTTTTTTTTTTTTTTTTTTTTTTTTTGCCGCTATTTTGCTCT | (SEQ ID No. 11) |
| FEAF10: | TTTTTTTTTTTTTTTTTTTTTTTTTTTTTTTTTTTTTTTTTGCCGCTATTTTGCTCT | (SEQ ID No. 12) |
| FEAF11: | TTTTTTTTTTTTTTTTTTTTTTTTTTTTTTTTTTTTTTTTTTTTTGCCGCTATTTTGCTCT | (SEQ ID No. 13) |
| FEAF12: | TTTTTTCGATCTCCAGGCTTGTTG | (SEQ ID No. 14) |
| FEAF13: | TTTTTTTTTTCGATCTCCAGGCTTGTTG | (SEQ ID No. 15) |
| FEAF14: | TTTTTTTTTTTTTTCGATCTCCAGGCTTGTTG | (SEQ ID No. 16) |
| FEAF15: | TTTTTTTTTTTTTTTTTTCGATCTCCAGGCTTGTTG | (SEQ ID No. 17) |
| FEAF16: | TTTTTTTTTTTTTTTTTTTTTTCGATCTCCAGGCTTGTTG | (SEQ ID No. 18) |
| FEAF17: | TTTTTTTTTTTTTTTTTTTTTTTTTTCGATCTCCAGGCTTGTTG | (SEQ ID No. 19) |
| FEAF18: | TTTTTTTTTTTTTTTTTTTTTTTTTTTTTTCGATCTCCAGGCTTGTTG | (SEQ ID No. 20) |
| FEAF19: | TTTTTTTTTTTTTTTTTTTTTTTTTTTTTTTTTTCGATCTCCAGGCTTGTTG | (SEQ ID No. 21) |
| FEAF20: | TTTTTTTTTTTTTTTTTTTTTTTTTTTTTTTTTTTTTTCGATCTCCAGGCTTGTTG | (SEQ ID No. 22) |
| FEAF21: | TTTTTTTTTTTTTTTTTTTTTTTTTTTTTTTTTTTTTTTTTTCGATCTCCAGGCTTGTTG | (SEQ ID No. 23) |
| FEAF22: | TTTTTTTTTTTTTTTTTTTTTTTTTTTTTTTTTTTTTTTTTTTTTTCGATCTCCAGGCTTGTTG | (SEQ ID No. 24) |

TABLE 1-continued

List of primers used in this experiment

List of SCAR primers specific to C-genome amplify the two bases deletion position:

| | | |
|---|---|---|
| Reverse: FE42A (labeled): | GACCATCTTTAACCCTAAAACC | (SEQ ID No. 25) |
| Forward: FE42D: | CAATGTCAAAGCTTCAA | (SEQ ID No. 26) |
| Forward: FE42D1: | GGCTCTAAACAATGTCAAAGC | (SEQ ID No. 27) |
| Forward: FE42E1: | TGCAGTTTGGGTGGCTCT | (SEQ ID No. 28) |
| Forward: FE42F: | GTGTAACAGTGCAGTTTGGG | (SEQ ID No. 29) |
| Forward: FE42F1: | GGCTTTAAGTGTAACAGTGC | (SEQ ID No. 30) |
| Forward: FE42G1: | TTAGGGTCAGGCTTTAAG | (SEQ ID No. 31) |
| Forward: FE42J: | GGTAATAAAGTTTGGCAG | (SEQ ID No. 32) |
| Forward: FE42K: | GCAAAAGGAAGGATGAAG | (SEQ ID No. 33) |
| Forward: FE41: | GGCATACATAGAAGCAAAAG | (SEQ ID No. 34) |
| Forward: FE42L: | TGGTATGAGTTGGCATAC | (SEQ ID No. 35) |
| Forward: FE42M1: | CTAGCTCAATATGGTATGAG | (SEQ ID No. 36) |
| Forward: FE42M: | GGAAACACTTCATCTAGCTC | (SEQ ID No. 37) |
| Forward: FE42N1: | CATAGATTTGGAAACACTTC | (SEQ ID No. 38) |
| Forward: FE42N2: | CAACGTTACATAGATTTGG | (SEQ ID No. 39) |
| Forward: FE42N: | GGCATCAAGATCAACGTTAC | (SEQ ID No. 40) |
| Forward: FE42O: | TCGATGTAGAGGCATCAAG | (SEQ ID No. 41) |
| Forward: FE42P: | CCTAGCACCGATCGATGTAG | (SEQ ID No. 42) |
| Forward: FE42Q: | AGAACCTAGGCCTAGCACCG | (SEQ ID No. 43) |
| Forward: FE42R: | GTGCTAGAGAAGAACCTAGG | (SEQ ID No. 44) |
| Forward: FE42S: | AGCCGTGATTGATGTGCTAG | (SEQ ID No. 45) |

TABLE 2

Segregation for erucic acid in the $F_2$ and $BC_1$ generations of *B. napus*.

| Generation | Segregation ratio | Erucic acid content 7-45% | Erucic acid content 0-1% | $\chi^2$ | P |
|---|---|---|---|---|---|
| $F_2$ | 15:1 | 259 | 20 | 0.401 | 0.5-0.7 |
| $BC_1$ | 3:1 | 120 | 39 | 0.019 | 0.7-0.9 |

TABLE 3

Erucic acid content in different genotypic class of $F_2$ and $BC_1$ populations. The genotyping were done on the basis of SNP and SCAR markers detected in ABI 3100 Genetic Analyzer as shown in FIG. 2 and 3b.

| Generation/Genotypes | Expected genotypic ratio | Number of individuals | Mean Erucic acid (%) and SD* |
|---|---|---|---|
| $F_2$ | | | |
| E1E1E2E2 | 1 | 10 | 41.2 ± 0.83 |
| E1E1E2e2 | 2 | 22 | 34.5 ± 2.21 |
| E1E1e2e2 | 1 | 11 | 24.2 ± 1.88 |
| E1e1E2E2 | 2 | 23 | 34.3 ± 1.94 |
| E1e1E2e2 | 4 | 37 | 24.1 ± 2.31 |
| E1e1e2e2 | 2 | 19 | 12.8 ± 2.00 |
| e1e1E2E2 | 1 | 11 | 22.9 ± 1.73 |
| e1e1E2e2 | 2 | 24 | 12.0 ± 1.91 |
| e1e1e2e2 | 1 | 13 | 0.26 ± 0.29 |
| | | $\chi^2$ ($F_2$) = 2.358 (P = 0.90-0.95) | |
| $BC_1$ | | | |
| E1e1E2e2 | 1 | 26 | 19.8 ± 1.90 |
| E1e1e2e2 | 1 | 23 | 10.5 ± 1.61 |
| e1e1E2e2 | 1 | 22 | 10.4 ± 1.11 |
| e1e1e2e2 | 1 | 32 | 0.18 ± 0.22 |
| | | $\chi^2$ ($BC_1$) = 2.358 (P = 0.5-0.7) | |

*Standard deviation

The invention claimed is:

1. A method of identifying the erucic acid locus in a *Brassica* plant, wherein the erucic acid locus is a high erucic acid content locus or a low erucic acid content locus, comprising:
    admixing a primer consisting of SEQ ID NO: 25 and a primer selected from SEQ ID Nos. 26-45 with a DNA sample from a *Brassica* plant under conditions suitable for nucleic acid extension; and
    analyzing the extension product produced from a given DNA sample, wherein a single extension product having a first length indicates that the erucic acid locus is homozygous high erucic acid content, a single extension product having a second length indicates that the erucic acid locus is homozygous low erucic acid content and two extension products of both first and second lengths indicates that the erucic acid locus is heterozygous for high and low erucic acid content, and wherein the extension product having a first length is 2 bases longer than the extension product having a second length.

* * * * *

SEQUENCE LISTING

```
<160> NUMBER OF SEQ ID NOS: 49

<210> SEQ ID NO 1
<211> LENGTH: 21
<212> TYPE: DNA
<213> ORGANISM: Artificial
<220> FEATURE:
<223> OTHER INFORMATION: primer

<400> SEQUENCE: 1
ctcattcccg agaaacactg a                                      21

<210> SEQ ID NO 2
<211> LENGTH: 20
<212> TYPE: DNA
<213> ORGANISM: Artificial
<220> FEATURE:
<223> OTHER INFORMATION: primer

<400> SEQUENCE: 2
ctacgatctc caggcttgtt                                        20

<210> SEQ ID NO 3
<211> LENGTH: 21
<212> TYPE: DNA
<213> ORGANISM: Artificial
<220> FEATURE:
<223> OTHER INFORMATION: primer

<400> SEQUENCE: 3
tttttgccgc tattttgctc t                                      21

<210> SEQ ID NO 4
<211> LENGTH: 26
<212> TYPE: DNA
<213> ORGANISM: Artificial
<220> FEATURE:
<223> OTHER INFORMATION: primer
```

```
<400> SEQUENCE: 4
tttttttttt gccgctattt tgctct                                      26

<210> SEQ ID NO 5
<211> LENGTH: 31
<212> TYPE: DNA
<213> ORGANISM: Artificial
<220> FEATURE:
<223> OTHER INFORMATION: primer

<400> SEQUENCE: 5
tttttttttt ttttgccgc tattttgctc t                                 31

<210> SEQ ID NO 6
<211> LENGTH: 36
<212> TYPE: DNA
<213> ORGANISM: Artificial
<220> FEATURE:
<223> OTHER INFORMATION: primer

<400> SEQUENCE: 6
tttttttttt tttttttttt gccgctattt tgctct                           36

<210> SEQ ID NO 7
<211> LENGTH: 41
<212> TYPE: DNA
<213> ORGANISM: Artificial
<220> FEATURE:
<223> OTHER INFORMATION: primer

<400> SEQUENCE: 7
tttttttttt tttttttttt ttttgccgc tattttgctc t                      41

<210> SEQ ID NO 8
<211> LENGTH: 46
<212> TYPE: DNA
<213> ORGANISM: Artificial
<220> FEATURE:
<223> OTHER INFORMATION: primer

<400> SEQUENCE: 8
tttttttttt tttttttttt tttttttttt gccgctattt tgctct                46

<210> SEQ ID NO 9
<211> LENGTH: 51
<212> TYPE: DNA
<213> ORGANISM: Artificial
<220> FEATURE:
<223> OTHER INFORMATION: primer

<400> SEQUENCE: 9
tttttttttt tttttttttt tttttttttt ttttgccgc tattttgctc t           51

<210> SEQ ID NO 10
<211> LENGTH: 56
<212> TYPE: DNA
<213> ORGANISM: Artificial
<220> FEATURE:
<223> OTHER INFORMATION: primer

<400> SEQUENCE: 10
tttttttttt tttttttttt tttttttttt tttttttttt gccgctattt tgctct     56

<210> SEQ ID NO 11
```

<210> SEQ ID NO 11
<211> LENGTH: 61
<212> TYPE: DNA
<213> ORGANISM: Artificial
<220> FEATURE:
<223> OTHER INFORMATION: primer

<400> SEQUENCE: 11
tttttttttt tttttttttt tttttttttt tttttttttt ttttttgccgc tattttgctc    60 t                                                                    61

<210> SEQ ID NO 12
<211> LENGTH: 66
<212> TYPE: DNA
<213> ORGANISM: Artificial
<220> FEATURE:
<223> OTHER INFORMATION: primer

<400> SEQUENCE: 12
tttttttttt tttttttttt tttttttttt tttttttttt tttttttttt gccgctattt    60
tgctct                                                               66

<210> SEQ ID NO 13
<211> LENGTH: 71
<212> TYPE: DNA
<213> ORGANISM: Artificial
<220> FEATURE:
<223> OTHER INFORMATION: primer

<400> SEQUENCE: 13
tttttttttt tttttttttt tttttttttt tttttttttt tttttttttt tttttgccgc    60
tattttgctc t                                                         71

<210> SEQ ID NO 14
<211> LENGTH: 24
<212> TYPE: DNA
<213> ORGANISM: Artificial
<220> FEATURE:
<223> OTHER INFORMATION: primer

<400> SEQUENCE: 14 tttttttcgat ctccaggctt gttg                                          24

<210> SEQ ID NO 15
<211> LENGTH: 29
<212> TYPE: DNA
<213> ORGANISM: Artificial
<220> FEATURE:
<223> OTHER INFORMATION: primer

<400> SEQUENCE: 15
tttttttttt tcgatctcca ggcttgttg                                      29

<210> SEQ ID NO 16
<211> LENGTH: 33
<212> TYPE: DNA
<213> ORGANISM: Artificial
<220> FEATURE:
<223> OTHER INFORMATION: primer

<400> SEQUENCE: 16
tttttttttt ttttttcgatc tccaggcttg ttg                                33

<210> SEQ ID NO 17
<211> LENGTH: 37

<212> TYPE: DNA
<213> ORGANISM: Artificial
<220> FEATURE:
<223> OTHER INFORMATION: primer

<400> SEQUENCE: 17
tttttttttt ttttttttc gatctccagg cttgttg                              37

<210> SEQ ID NO 18
<211> LENGTH: 42
<212> TYPE: DNA
<213> ORGANISM: Artificial
<220> FEATURE:
<223> OTHER INFORMATION: primer

<400> SEQUENCE: 18
tttttttttt tttttttttt ttttcgatct ccaggcttgt tg                       42

<210> SEQ ID NO 19
<211> LENGTH: 48
<212> TYPE: DNA
<213> ORGANISM: Artificial
<220> FEATURE:
<223> OTHER INFORMATION: primer

<400> SEQUENCE: 19
tttttttttt tttttttttt tttttttttt cgatctccag gcttgttg                 48

<210> SEQ ID NO 20
<211> LENGTH: 53
<212> TYPE: DNA
<213> ORGANISM: Artificial
<220> FEATURE:
<223> OTHER INFORMATION: primer

<400> SEQUENCE: 20
tttttttttt tttttttttt tttttttttt ttttcgatc tccaggcttg ttg            53

<210> SEQ ID NO 21
<211> LENGTH: 58
<212> TYPE: DNA
<213> ORGANISM: Artificial
<220> FEATURE:
<223> OTHER INFORMATION: primer

<400> SEQUENCE: 21
tttttttttt tttttttttt tttttttttt tttttttttt cgatctccag gcttgttg     58

<210> SEQ ID NO 22
<211> LENGTH: 63
<212> TYPE: DNA
<213> ORGANISM: Artificial
<220> FEATURE:
<223> OTHER INFORMATION: primer

<400> SEQUENCE: 22
tttttttttt tttttttttt tttttttttt tttttttttt ttttcgatc tccaggcttg    60 ttg                                                                   63

<210> SEQ ID NO 23
<211> LENGTH: 68
<212> TYPE: DNA
<213> ORGANISM: Artificial
<220> FEATURE:
<223> OTHER INFORMATION: primer

```
<400> SEQUENCE: 23
tttttttttt tttttttttt tttttttttt tttttttttt tttttttttt cgatctccag    60
gcttgttg                                                             68

<210> SEQ ID NO 24
<211> LENGTH: 73
<212> TYPE: DNA
<213> ORGANISM: Artificial
<220> FEATURE:
<223> OTHER INFORMATION: primer

<400> SEQUENCE: 24
tttttttttt tttttttttt tttttttttt tttttttttt tttttttttt tttttcgatc    60
tccaggcttg ttg                                                       73

<210> SEQ ID NO 25
<211> LENGTH: 22
<212> TYPE: DNA
<213> ORGANISM: Artificial
<220> FEATURE:
<223> OTHER INFORMATION: primer

<400> SEQUENCE: 25
gaccatcttt aaccctaaaa cc                                             22

<210> SEQ ID NO 26
<211> LENGTH: 17
<212> TYPE: DNA
<213> ORGANISM: Artificial
<220> FEATURE:
<223> OTHER INFORMATION: primer

<400> SEQUENCE: 26
caatgtcaaa gcttcaa                                                   17

<210> SEQ ID NO 27
<211> LENGTH: 21
<212> TYPE: DNA
<213> ORGANISM: Artificial
<220> FEATURE:
<223> OTHER INFORMATION: primer

<400> SEQUENCE: 27
ggctctaaac aatgtcaaag c                                              21

<210> SEQ ID NO 28
<211> LENGTH: 18
<212> TYPE: DNA
<213> ORGANISM: Artificial
<220> FEATURE:
<223> OTHER INFORMATION: primer

<400> SEQUENCE: 28
tgcagtttgg gtggctct                                                  18

<210> SEQ ID NO 29
<211> LENGTH: 20
<212> TYPE: DNA
<213> ORGANISM: Artificial
<220> FEATURE:
<223> OTHER INFORMATION: primer

<400> SEQUENCE: 29
gtgtaacagt gcagtttggg                                                20
```

<210> SEQ ID NO 30
<211> LENGTH: 20
<212> TYPE: DNA
<213> ORGANISM: Artificial
<220> FEATURE:
<223> OTHER INFORMATION: primer

<400> SEQUENCE: 30
ggctttaagt gtaacagtgc                                               20

<210> SEQ ID NO 31
<211> LENGTH: 18
<212> TYPE: DNA
<213> ORGANISM: Artificial
<220> FEATURE:
<223> OTHER INFORMATION: primer

<400> SEQUENCE: 31
ttagggtcag gctttaag                                                 18

<210> SEQ ID NO 32
<211> LENGTH: 18
<212> TYPE: DNA
<213> ORGANISM: Artificial
<220> FEATURE:
<223> OTHER INFORMATION: primer

<400> SEQUENCE: 32
ggtaataaag tttggcag                                                 18

<210> SEQ ID NO 33
<211> LENGTH: 18
<212> TYPE: DNA
<213> ORGANISM: Artificial
<220> FEATURE:
<223> OTHER INFORMATION: primer

<400> SEQUENCE: 33
gcaaaaggaa ggatgaag                                                 18

<210> SEQ ID NO 34
<211> LENGTH: 20
<212> TYPE: DNA
<213> ORGANISM: Artificial
<220> FEATURE:
<223> OTHER INFORMATION: primer

<400> SEQUENCE: 34
ggcatacata gaagcaaaag                                               20

<210> SEQ ID NO 35
<211> LENGTH: 18
<212> TYPE: DNA
<213> ORGANISM: Artificial
<220> FEATURE:
<223> OTHER INFORMATION: primer

<400> SEQUENCE: 35
tggtatgagt tggcatac                                                 18

<210> SEQ ID NO 36
<211> LENGTH: 20
<212> TYPE: DNA
<213> ORGANISM: Artificial
<220> FEATURE:

```
<223> OTHER INFORMATION: primer

<400> SEQUENCE: 36
ctagctcaat atggtatgag                                               20

<210> SEQ ID NO 37
<211> LENGTH: 20
<212> TYPE: DNA
<213> ORGANISM: Artificial
<220> FEATURE:
<223> OTHER INFORMATION: primer

<400> SEQUENCE: 37
ggaaacactt catctagctc                                               20

<210> SEQ ID NO 38
<211> LENGTH: 20
<212> TYPE: DNA
<213> ORGANISM: Artificial
<220> FEATURE:
<223> OTHER INFORMATION: primer

<400> SEQUENCE: 38
catagatttg gaaacacttc                                               20

<210> SEQ ID NO 39
<211> LENGTH: 19
<212> TYPE: DNA
<213> ORGANISM: Artificial
<220> FEATURE:
<223> OTHER INFORMATION: primer

<400> SEQUENCE: 39
caacgttaca tagatttgg                                                19

<210> SEQ ID NO 40
<211> LENGTH: 20
<212> TYPE: DNA
<213> ORGANISM: Artificial
<220> FEATURE:
<223> OTHER INFORMATION: primer

<400> SEQUENCE: 40
ggcatcaaga tcaacgttac                                               20

<210> SEQ ID NO 41
<211> LENGTH: 19
<212> TYPE: DNA
<213> ORGANISM: Artificial
<220> FEATURE:
<223> OTHER INFORMATION: primer

<400> SEQUENCE: 41
tcgatgtaga ggcatcaag                                                19

<210> SEQ ID NO 42
<211> LENGTH: 20
<212> TYPE: DNA
<213> ORGANISM: Artificial
<220> FEATURE:
<223> OTHER INFORMATION: primer

<400> SEQUENCE: 42
cctagcaccg atcgatgtag                                               20
```

<210> SEQ ID NO 43
<211> LENGTH: 20
<212> TYPE: DNA
<213> ORGANISM: Artificial
<220> FEATURE:
<223> OTHER INFORMATION: primer

<400> SEQUENCE: 43
agaacctagg cctagcaccg                                                 20

<210> SEQ ID NO 44
<211> LENGTH: 20
<212> TYPE: DNA
<213> ORGANISM: Artificial
<220> FEATURE:
<223> OTHER INFORMATION: primer

<400> SEQUENCE: 44
gtgctagaga agaacctagg                                                 20

<210> SEQ ID NO 45
<211> LENGTH: 20
<212> TYPE: DNA
<213> ORGANISM: Artificial
<220> FEATURE:
<223> OTHER INFORMATION: primer

<400> SEQUENCE: 45
agccgtgatt gatgtgctag                                                 20

<210> SEQ ID NO 46
<211> LENGTH: 177
<212> TYPE: DNA
<213> ORGANISM: Brassica rapa

<400> SEQUENCE: 46
aaattatctt attccggtca tgttggcctt aactaaactt ccacacattt gtttactgat     60
attcgagtat aaactttgcg ggaaaactca ttcccgagaa acactgatcc cataattagt    120
cagagtctat gtcggtttag cctatcactg ctaagtacaa aaattctctc gaattca       177

<210> SEQ ID NO 47
<211> LENGTH: 96
<212> TYPE: DNA
<213> ORGANISM: Brassica rapa

<400> SEQUENCE: 47
gtatgtatct cttatttaca tgaaattttt aaacgcctaa cactatgacg tcatatccta     60
aatcaaacaa ctaaaacccc gagttctatc atttat                               96

<210> SEQ ID NO 48
<211> LENGTH: 176
<212> TYPE: DNA
<213> ORGANISM: Brassica oleracea

<400> SEQUENCE: 48
atgtggtgac acgtggtttg aaacccacca ataatcgat cacaaaaaac ctaagttaag     60
gatcggtaat aacctttcta attaattttg atttaattaa atcactcttt ttatttataa    120
accccactaa attatgcgat attgattgtc taagtacaaa aattctctcg aattca        176

<210> SEQ ID NO 49
<211> LENGTH: 120
<212> TYPE: DNA

```
<213> ORGANISM: Brassica oleracea

<400> SEQUENCE: 49
gtatgtatct cttagaccat ctttaaccct aaaacccttt ttgagatcct taagaaaatt      60
ttaataataa attaaacctt aagtggggtt aaggatctct gttaagaaac ttccattttt     120
```